Figure 1:
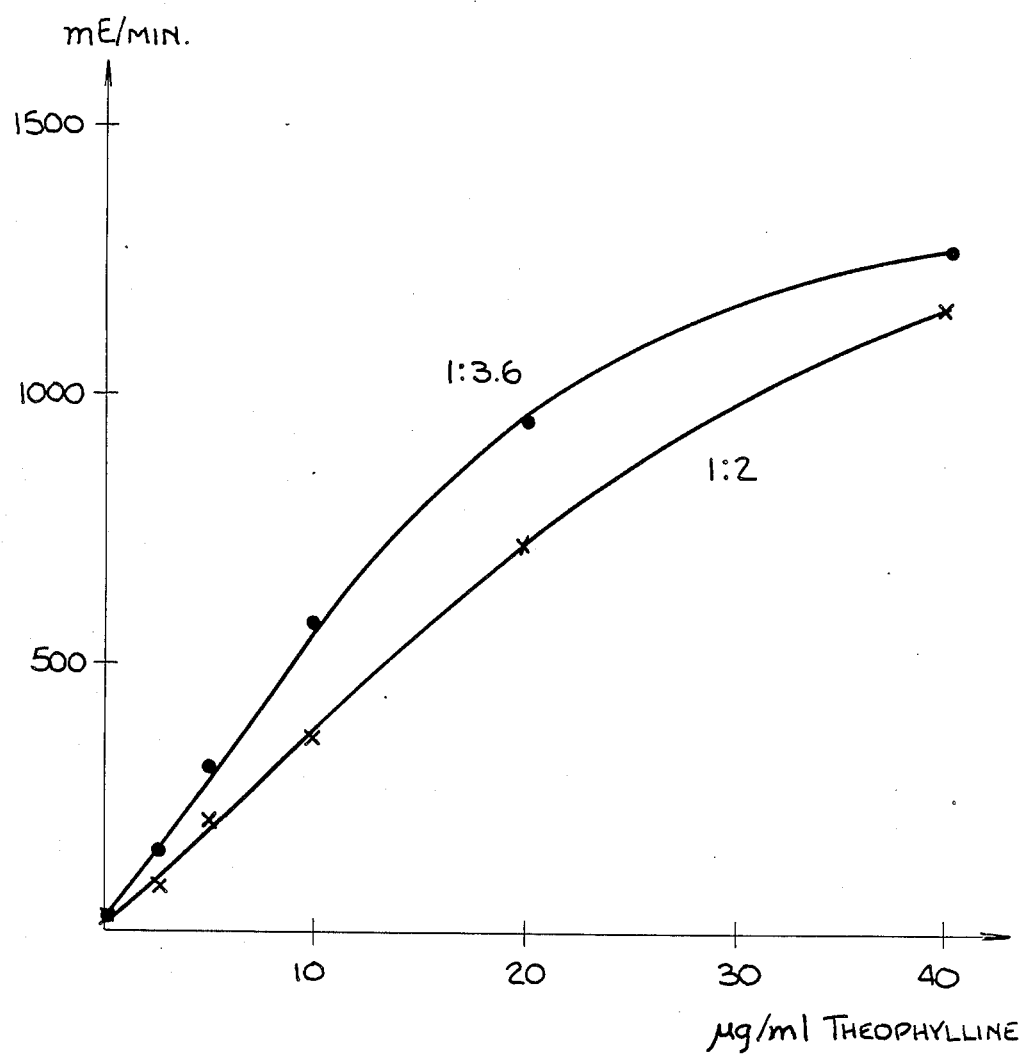

| United States Patent [19] | [11] Patent Number: 4,820,633 |
| Herrmann | [45] Date of Patent: Apr. 11, 1989 |

[54] PROCESS FOR PRODUCTION OF AN IMMUNE REACTIVE, POROUS CARRIER MATERIAL FOR HETEROGENEOUS IMMUNOLOGICAL ANALYSIS

[75] Inventor: Uwe Herrmann, Kirchheim, Fed. Rep. of Germany

[73] Assignee: Boehringer Mannheim GmbH, Mannheim, Fed. Rep. of Germany

[21] Appl. No.: 59,066

[22] Filed: Jun. 8, 1987

[30] Foreign Application Priority Data

Jun. 20, 1986 [DE] Fed. Rep. of Germany ....... 3620653

[51] Int. Cl.$^4$ ................. G01N 33/543; G01N 33/545
[52] U.S. Cl. ........................................ 435/7; 436/512; 436/525; 436/527; 436/530; 436/531
[58] Field of Search ................... 435/7; 436/512, 525, 436/527, 530, 531

[56] References Cited

U.S. PATENT DOCUMENTS 4,012,285  3/1977  Pfleiderer ..................... 436/534 X
4,604,365  8/1986  O'Neill ............................. 436/528

Primary Examiner—Sidney Marantz
Attorney, Agent, or Firm—Felfe & Lynch

[57] ABSTRACT

Process for the production of an immune-reactive, porous carrier material for heterogeneous immunological analysis by application to a carrier material of a solution of a receptor and of a component precipitating this immunologically, incubation of the carrier material impregnated with these solutions for the immune precipitation, optional washing and subsequent drying of the impregnated carrier material, wherein the concentrations of the receptor and of the component are so chosen that, in the case of the impregnation, their molar ratio is greater than the ratio defined by the Heidelberger maximum. Also a carrier material for heterogeneous, immunological analysis, wherein it contains a receptor and an immunologically precipitating component in a molar ratio which is greater than the ratio defined by the Heidelbeger maximum.

19 Claims, 3 Drawing Sheets

PROCESS FOR PRODUCTION OF AN IMMUNE REACTIVE, POROUS CARRIER MATERIAL FOR HETEROGENEOUS IMMUNOLOGICAL ANALYSIS

The present invention is concerned with a carrier material for heterogeneous immunological analysis, with a process for the preparation thereof and with the use thereof.

By means of heterogeneous immunological analysis, there can be determined immunologically active receptors, for example antibodies, antigens or haptens. Such processes are known, for example, as competitive tests, IEMA tests and sandwich tests. A feature common to these processes is that one of the reaction components is immobilized on an insoluble carrier material in such a manner that it cannot be washed off.

The fixing of a receptor on to an insoluble carrier material can take place by covalent or adsorptive binding (see Methods in Enzymology, 73b, pp. 203-244/1981 and B.E.T. Maggio "Enzyme Immunoassay", pub. CAC Press, Florida, U.S.A., 1980, especially pages 175 to 178).

Not only the covalent but also the adsorptive binding of receptors on to the solid phase has serious disadvantages. The chemical change on the receptor necessary in the case of covalent binding also brings about, in all cases, a change of the biological activity of the receptor. A disadvantage of the adsorptive binding is that the loading density is very low and, upon washing the carrier material, the desorption of the receptor cannot be completely prevented.

A further fixing method of receptors on to a carrier material is the immune precipitate formation (cf., for example, PCT-WO 82/02601 and U.S. Pat. No. 3,888,629). The receptor to be immobilized is hereby brought together with a precipitating component on a carrier material and an immune precipitation is carried out. Between the receptor and its immunological partner, there is formed, in the precipitation thereof, a network which is embedded in the interior and/or on the surface of the carrier material and can no longer be dissolved off by washing. In this way, there is achieved a high loading density without chemical modification of the receptor to be immobilized.

However, the known processes for immune precipitation have the disadvantage that the receptor is hereby non-uniformly distributed over the carrier material. This disadvantage is especially serious when the carrier material is to be used, for example, for the purpose of the quantitative analysis of low concentrations of haptens or proteins. This disadvantage can be overcome by the disclosure in assignee's copending Federal Republic of Germany patent application No. P 34 46 636, the total disclosure of which is incorporated into the present application.

In this patent application No. P 34 46 636, there is described a process for the production of an immune-reactive porous carrier material by application of a solution of a first component of an immune reaction and of a second component of an immune reaction precipitating therewith, incubation of the carrier material impregnated with the solutions for the immune precipitation, possible washing and subsequent drying of the impregnated carrier material, wherein a solution of both components of the immune reaction is prepared which contains an inhibitor for the immune precipitation, the carrier material is impregnated with this solution and then the immune precipitation is initiated by removing the inhibitor or by removal of its inhibiting action.

However, we have found that in the case of the use of carrier materials which contain receptors immobilized by immune precipitation, in many cases the precision and the linearity of the calibration curve (measurement signal/concentration) are not satisfactory.

Therefore, it is an object of the present invention to provide an improved carrier material which contains an immobilized receptor in the immune precipitate with which, in heterogeneous immunological tests, an improved precision and a greater linearity of the calibration curve can be achieved.

Thus, according to the present invention, there is provided a process for the production of an immune-reactive, porous carrier material for heterogeneous immunological analysis by application to a carrier material of a solution of a receptor and of an immune precipitating component precipitating that receptor immunologically on to said carrier, incubation of the carrier material impregnated with these solutions for the immune precipitation, optional washing and subsequent drying of the impregnated carrier material, wherein the concentrations of the receptor and of the component are so chosen that, in the case of the impregnation, their molar ratio is greater than the ratio defined by the Heidelberger maximum.

Surprisingly, we have found that the ratio of receptor and immune-precipitating component has a substantial influence on the precision and the linearity of the calibration curve. It is thereby especially surprising that with the concentration ratios favorable for the immune precipitation, such as are present, for example, at the Heidelberger maximum, the optimum precision and linearity of the calibration curve is not achieved.

The molar concentrations of the receptor and of the immune-reactive component are so chosen that their ratio is greater than the ratio defined by the Heidelberger maximum. The ratio of the Heidelberger maximum can previously be easily ascertained by turbidity tests. A corresponding turbidity curve is to be found, for example, in "Methods of Immunology and Immunochemistry", Volume III, pub. Academic Press, chapter 13, page 10, 1971. In the production of such a curve, the turbidity is plotted which is obtained in the case of a constant amount of one of the two reaction components with increasing amounts of the other reaction component. The turbidity maximum is the Heidelberger maximum.

Usually, the Heidelberger maximum is about 1:3.5 for the molar ratio of receptor to precipitating component for purified materials. The advantageous action according to the present invention is then achieved when this ratio is greater. It is preferred to use a ratio greater than or equal to 1:3. It is especially preferred to use a ratio greater than 1:2.5, as well as smaller than 1:1.

The receptor and precipitating components can be applied to the carrier material either sequentially or simultaneously. In the case of the sequential method, the carrier material is first impregnated either with the receptor or with the precipitating component and subsequently the corresponding other component is applied thereto. However, it is preferred to carry out the impregnation of the carrier material simultaneously. Especially preferably, the impregnation is carried out in the presence of an inhibiting material, as is described in Federal Republic of Germany patent application No. P 34 46 636. There is hereby preferred not only the "one-step process" but also the "two-step process". In order to achieve a cross-linking of the receptor and immune-precipitating component, both of them must be at least bivalent with regard to their immunological bindability with one another. Thus, for example, an immune precipitate can be formed between two bivalent antibodies or antibody fragments or one antibody and one haptenized protein.

Consequently, as receptors there can be used immunologically at least bivalent substances, for example antibodies and bivalent fragments thereof, which can be not only monoclonal but also polyclonal, as well as other proteins. Antigens and haptenized proteins can also be used. If, for an immunological determination, an immobilized hapten is to be used, then a polyhapten is preferably used as receptor. Thus, for example, several hapten molecules, which in this case can also be monovalent, are thereby bound to a bi- or polvalent carrier protein, for example an antibody or serum albumin. In this way, an immune precipitation can also be achieved for monovalent haptens.

The immune-precipitating component of the reaction must be chosen corresponding to the receptor. For this purpose, there is preferably used an antibody which is bivalent and directed against the receptor. Especially preferably, there is used an antibody which has an affinity to the receptor which is as high as possible in order that the fixing of the immune precipitate to the carrier material is as firm as possible.

As carrier materials, within the scope of the present invention there can be used the conventional solid carriers for immune-reactive substances. Such a carrier material, which is frequently also called a matrix, can include, for example, glass, synthetic resin, paper, porous metal or the like, provided that the carrier material is sufficiently permeated by interconnected, liquid-permeable hollow spaces. Natural, synthetic, organic and inorganic polymers can also be used. In addition, fibre-like, sponge-like and sintered substances can be used. The reagent carriers can be planar or particulate or can be used in some other form. Especially preferred as reagent carriers are planar, porous carriers, for example papers, foamed material films, glass mats and the like.

The use of an immune-reactive carrier material produced according to the present invention can take place in the scope of a heterogeneous enzyme immunoassay in that, for example, hapten (H) or protein (P) which is present in a sample, such as a buffer solution, serum, plasma, urine, culture supernatant or the like, is mixed with a labelled binder (B). As binders, there can be used, inter alia, antibodies, Fab⁻ fragments and Fab fragments, as well as ligands, which react specifically with the hapten or protein. For labelling the binder, there can be used, for example, an enzyme, a fluorescent label or a radio-isotope. In the following Examples, $\beta$-galactosidase is used. The amount of binder added can be molar or also in excess or in insufficiency to the hapten or protein present in the sample.

This mixture is incubated for a constant period of time, during which the complexes H-B or P-B are formed. After the expiry of this period of time, three species are present in the reaction mixture, namely, the complex consisting of hapten/protein and binder (H-B, P-B), residual free hapten/protein (H/P) and residual free binder (B).

The separation of these species takes place in a second step by means of immunosorption. For this purpose, the mixture is applied to the immune precipitate solid phase produced according to the present invention which contains the hapten or antibody to be determined against the protein to be determined.

In the case of the hapten test, the free binder, but not the binder saturated with hapten, is bound to the solid phase. Consequently, the supernatant or the eluate of the solid phase contains the binder saturated with the hapten of the sample. The quantitative determination of the hapten now takes place via the labelling of the binder and, in the following Examples, via the determination of $\beta$-galactosidase by means of o-nitrophenyl-$\beta$-D-galactoside or chlorophenol red-$\beta$-D-galactoside.

In the case of the protein test, the complex of protein and binder but not the free binder bind to the solid phase and residues of the free binder are removed by washing free from the immunosorbent produced according to the present invention. The quantitative determination of the protein takes place via the labelled binder, using the determination of $\beta$-galactosidase by means of o-nitrophenyl-$\beta$-D-galactoside or chlorophenol red-$\beta$-D-galactoside.

Another use is in competitive immune tests. The use of the immune-reactive carrier material produced according to the present invention can take place in such a manner that the analyte (hapten or protein), which is contained in the sample, is mixed with a constant amount of labelled analyte. The labelling can be with, for example, an enzyme, a fluorescent label, a radio-isotope or the like. This mixture is applied to the matrix. On the matrix, there is immobilised an antibody which is directed against the analyte. The mixture is incubated on the matrix for a definite period of time. During this time, not only unchanged analyte but also labelled analyte compete for the binding places on the matrix. The more analyte is present in the sample, the less labelled analyte is bound by the matrix and vice versa. At the end of the incubation phase, the liquid is removed from the porous matrix, for example by centrifuging. There is then determined the amount of labelled analyte either in the free phase or the amount of labelled analyte bound to the matrix.

Another use of the carrier material produced according to the present invention can take place in that the analyte (hapten or protein) is mixed with a constant amount of labelled antibody which is directed against the analyte. Possible types of labelling of the antibody are described hereinbefore. This mixture is either incubated for a definite period of time and then applied to the porous carrier material or, alternatively, immediately after mixing, is applied to the porous carrier material. When the analyte is a hapten, the carrier material contains the hapten to be detected or a derivative thereof in fixed form and if the analyte is a protein, the carrier material contains the protein to be detected or a derivative thereof, also in fixed form. If the first mixture is incubated before application to the carrier material, then the labelled antibody binds with the still free binding positions on the porous carrier material. If the mixture is immediately applied to the carrier material, then the analyte from the sample and the analyte fixed on the carrier material compete for the binding positions of the labelled antibody. At the end of the incubation phase, the liquid is removed from the porous carrier material and the amount of labelled antibody is determined either in the liquid phase or on the porous carrier material.

The following Examples are given for the purpose of illustrating the present invention:

Obtaining the materials used for the test and carrying out of the test (cf. also Federal Republic of Germany patent application No. P 34 46 636):

(A) Preparation of polyhaptens (PH):

The preparation of PH is known from the prior art. Thus, for example, a digoxin-PH or a diphenylhydantoin-PH can be obtained via reactive, asymmetrical dicarboxylic acids/activated hapten esters and binding thereof to a carrier protein.

The choice of the carrier proteins is not subject to any limitations insofar as a corresponding "precipitating" antibody is available or can be prepared.

The preparation of theophylline-PH can take place, for example, via theophylline-7-butyric acid (preparation according to European Pat. Specification No. 0013910) or via theophylline-7-propionic acid and coupling thereof to bovine serum albumin or some other protein (Nishikawa, Clin. Chim. Acta, 91, 59–65/1979; Erlenger, J. Biol. Chem., 228, 713–727/1975).

(B) Preparation of the binder (for example theophylline),

The preparation of the immunogen, as well as of the antiserum, can take place, for example, according to published Japanese Pat. Specification No. 57-099598, or U.S. Pat. Nos. 4,156,081; 4,302,438; 4,521,510 and 4,524,025, Res. Commun. Chem. Pathol. Pharmacol., 13, 497–505/1976 or Clin. Chim. Acta, 91 59–65/1979.

Insofar as an immunosorptive purification of antigen and antibody has taken place, as carrier there was used the "affinity adsorbent, glutaraldehyde activated" of Boehringer Mannheim GmbH (Order No. 665525), although additional materials could be used as well. For the Examples described hereinafter, according to the manufacturer's instructions for the antigen purification, a sheep antibody against rabbit IgG or a specific antibody against the hapten and for the antibody purification rabbit IgG was bound to the carrier. The carrying out of the immunosorption took place as described in the working instructions for the affinity adsorbent.

Antiserum directed against theophylline was purified by means of ammonium sulphate precipitation and passage over DEAE-cellulose for the IgG fraction. Papain cleavage was carried out according to the method of R. R. Porter, Biochem. J., 73, 119–126/1959.

The Fab fragments were separated from the nondigested IgG molecules and the Fc fragments by means of gel filtration over Sephadex G 100 and ion exchanger chromatography over DEAE-cellulose according to the method described in the literature (K. Malinowski and W. Manski; in "Meth. in Enzymology" J. J. Langone and H. Van Vunakis eds., pub. Academic Press. Vol. 73, 418–459/1981). The resulting Fab fraction was purified chromatographically and coupled to $\beta$-galactosidase according to the method of T. Kitiwaga in "Enzyme Immunoassay"; Ishikawa, T. Kawai and K. Miyai eds., pub. Igaku Shoin, Tokyo/New York, pp. 81–89/1981.

(C) Preparation of sheep antibody against rabbit or mouse IgG/Fc$\gamma$.

Rabbit serum or mouse serum was subjected to an ammonium sulphate precipitation. After passage over DEAE-cellulose and papain cleavage, gel and ion exchanger chromatography (see B), there were obtained the Fc fragments of the rabbit or mouse IgG's as immunogens.

The working up of the sheep antisera took place as described in (B).

(D) Carrying out of the test (for example theophylline).

Theophylline standards in a bovine serum albumin-containing buffer were diluted 1:100 with a 0.9% sodium chloride solution. To 200 $\mu$l. of diluted standard were added 200 $\mu$l. binder (1.6 U/ml., determined with o-nitrophenyl-$\beta$-D-galactoside), prepared as described in B), in phosphate-buffered saline (PBS) (pH 7.8) and incubated at 37° C.

Thereafter, 50 $\mu$l. of the mixture were applied to 1 cm$^2$ of the planar, immune-reactive carrier material. Incubation was carried out for a further 5 minutes at 37° C. and then centrifuged for 1 minute with an Eppendorf centrifuge.

The enzyme activity of the theophylline-binder complex in the free phase, was then measured kinetically at 410 nm by the addition of o-nitrophenyl-$\beta$-D-galactoside.

EXAMPLE 1

Production of theophylline-immune precipitate fleece.

As antigen, there was used polyhapten (PH), consisting of rabbit IgG and theophylline bound thereon (mole ratio of IgG:theophylline=1:3). The antigen was purified by means of ion exchanger chromatography.

As precipitating antibody (PAB), there was used polyclonal antibody directed against the Fc part of the rabbit IgG. The antibody was purified immunosoptively over a rabbit IgG column.

As porous carrier material (fleece), there was used a mixed fleece of regenerated cellulose and polyester (Kalff, Euskirchen, Germany) or of linters, regenerated cellulose and polyamide (Binzer, Hatzfeld, Eder, Germany).

Antigen (c=1.5 mg./ml.) and antibody (c=3 mg./ml. ratio 1:2 or 5.25 mg./ml. ratio 1:3.5 Heidelberger maximum) were separately taken up in 50 mM/l. acetic acid. They were then left to stand for 1 hour at ambient temperature. The solutions were mixed in a ratio of 1:1. In a following step, the solution was diluted with 4 parts of 50 mM/l. acetic acid + 100 mM/l. sodium chloride. The solution was again left to stand for 30 minutes at ambient temperature. Subsequently, the fleece was drawn through the impregnation solution and dried for 30 minutes at 30° C. in a circulating air drying cabinet.

The linearization of the calibration curve achieved is shown in FIG. 1 of the accompanying drawings. Compared with the concentration ratios at the Heidelberger maximum, with a ratio of the reaction components of 1:2, the precision of the measurement of a theophylline standard of 10 $\mu$g./ml. was improved from a 6% variation coefficient to an about 3% variation coefficient.

EXAMPLE 2

Plotting of a Heidelberger curve for theophylline.

Figure 2:
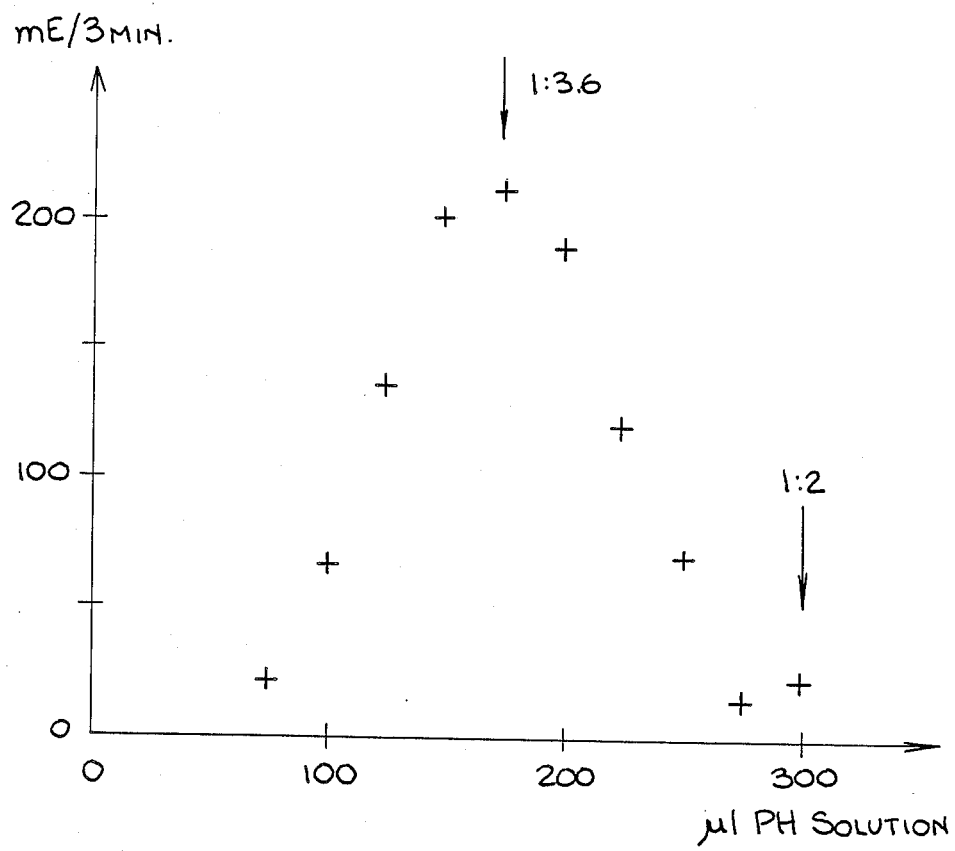

In cuvettes, there was, in each case, placed a constant volume of a known concentration of precipitating antibody, PAB, (4.1 mg./ml.) and mixed with increasing volumes of an antigen solution (PH solution) of known concentration (2.6 mg./ml.). The kinetics of the increase of turbidity were observed in a photometer at $\lambda$=340 nm. The Heidelberger maximum corresponds to the concentration ratio with the quickest change of turbidity. From FIG. 2 of the accompanying drawings, there is given the Heidelberger maximum at a ratio of:

$$\frac{c(PAB) \times v(PAB)}{c(PH) \times v(PH)} = \frac{4.1 \times 400}{2.6 \times 175} = \frac{1}{3.6} \text{ mg. } PAB/mg. \text{ } PH$$

EXAMPLE 3

Production of diphenylhydantoin (DPH)-immune precipitate.

Figure 3:
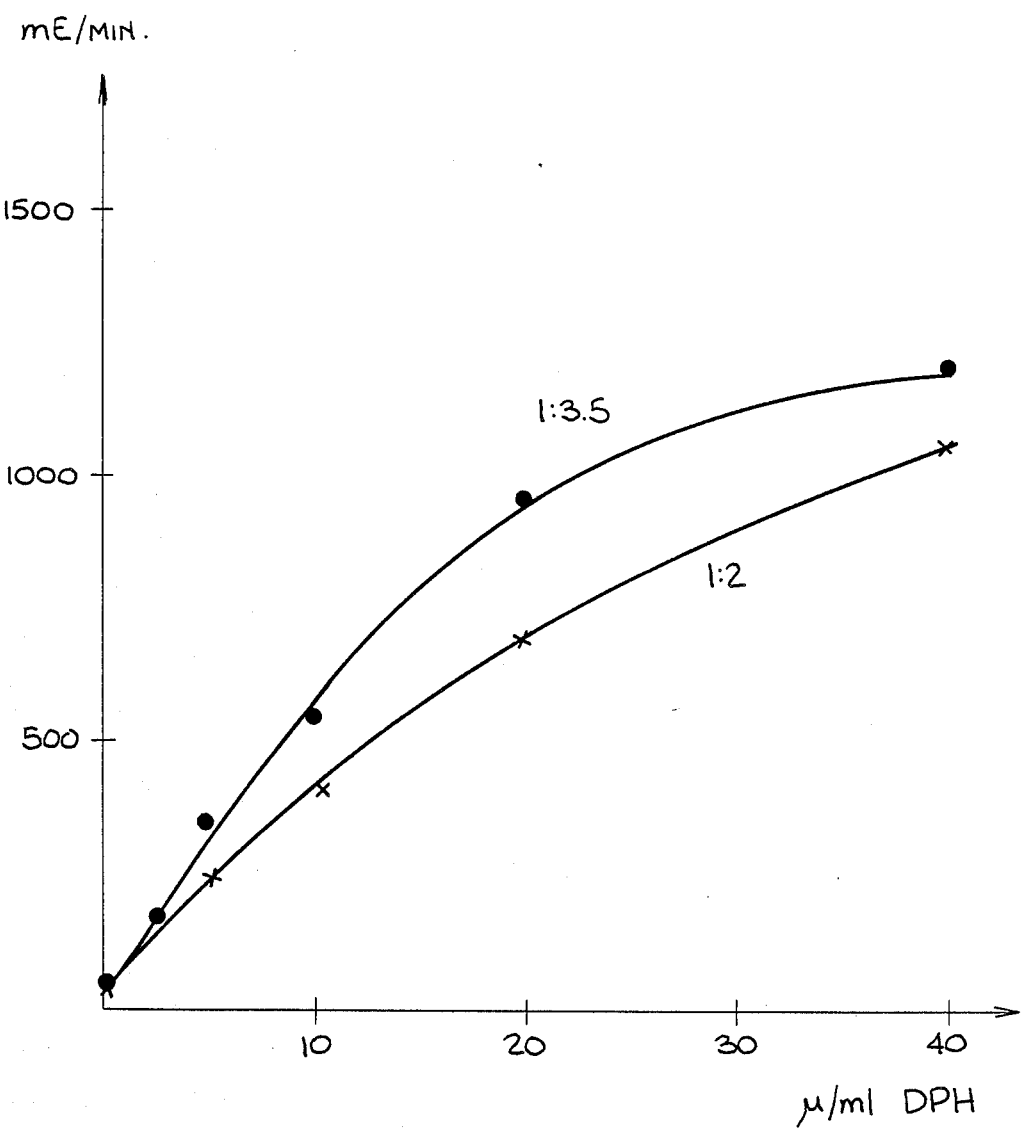

The production of diphenylhydantoin-immune precipitate fleece took place analogously to Example 1. The linearization of the calibration curve achieved is shown in FIG. 3 of the accompanying drawings.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. Process for preparing an immune reactive, porous carrier material for heterogeneous immunological analysis, comprising contacting a carrier material with a solution containing a receptor and a solution containing a receptor precipitating, immune-reactive component, incubating said solutions with said carrier to immunoprecipitate said receptor and to impregnate said carrier with said precipitating component and said receptor, wherein said impregnated receptor and said precipitating agent are present in said solutions in a molar ratio which is greater than the Heidelberger maximum.

2. Process as in claim 1, wherein the molar ratio of receptor:receptor precipitating immune reactive component is greater than or equal to 1:3.

3. Process as in claim 1, wherein the molar ratio of receptor:receptor precipitating immune reactive component is greater than 1:2.5.

4. Process as in claim 1, wherein the molar ratio of receptor:receptor precipitating immune reactive component is between 1:1 and 1:3.6.

5. Process as in claim 1, wherein one of said solutions contains an inhibitor of immune precipitation and said precipitation is inhibited until said inhibitor is removed from said solution or inhibition is prevented.

6. Process as in claim 1, wherein said receptor and receptor precipitaing immune reactive component are contacted to said carrier sequentially.

7. Process as in claim 1, wherein said receptor and receptor precipitating immune reactive component are contacted to said carrier simultaneously.

8. Process as in claim 1, wherein said receptor is a protein.

9. Process as in claim 8, wherein said protein is coupled to at least one hapten or antigen.

10. Process as in claim 8, wherein said protein is an antibody or fragment thereof.

11. Process as in claim 1, wherein said receptor is bivalent.

12. Process as in claim 1, wherein said receptor precipitating immune component is bivalent.

13. Process as in claim 1, wherein said receptor precipitating immune component is an antibody or fragment thereof.

14. Process of claim 1, wherein said carrier is selected from the group consisting of glass, paper, porous metal, and polymer.

15. Process of claim 1, wherein said carrier is fibrous, spongy, sintered, planar or porous.

16. Immune carrier produced by the process of claim 1.

17. Method for carrying out heterogeneous immunological analysis comprising contacting a liquid sample containing both an analyte to be determined and a labeled binder which specifically binds to said analyte to an immune carrier, said carrier containing a receptor which binds said labelled binder impregnated therein, wherein said receptor has been impregnated into said carrier by contacting said receptor with a receptor precipitating immune reactive component and said carrier to precipitate said receptor thereon, wherein said receptor and said receptor precipitating immune reactive component are contacted to said carrier in a molar ratio greater than the Heidelberger maximum, to complex free labelled binder to said receptor impregnated in said carrier, said contacting taking place under conditions favoring complexing a measurable component of said sample to said carrier and measuring said component in either said liquid or on said carrier as a direct or indirect measurement of said analyte.

18. Method of claim 17, wherein said measurable component is an enzyme, a fluorescent label, or a radioisotope.

19. Method of claim 17, wherein said measurable component is beta-galactosidase.

* * * * *